United States Patent
Heinen et al.

(10) Patent No.: US 9,364,802 B2
(45) Date of Patent: Jun. 14, 2016

(54) METHOD AND APPARATUS FOR THE INTERMIXING OF TWO FLUID STREAMS

(75) Inventors: Kerstin Heinen, Lorsch (DE); Stefan Karbach, Neustadt (DE); Burkhardt Dames, Heppenheim (DE); Wolfgang Haip, Hessheim (DE); Wolfgang Gerlinger, Limburgerhof (DE); Torsten Mattke, Freinsheim (DE)

(73) Assignee: BASF SE, Ludwigshafen (DE)

( * ) Notice: Subject to any disclaimer, the term of this patent is extended or adjusted under 35 U.S.C. 154(b) by 1142 days.

(21) Appl. No.: 13/407,363

(22) Filed: Feb. 28, 2012

(65) Prior Publication Data

US 2012/0226073 A1 Sep. 6, 2012

Related U.S. Application Data

(60) Provisional application No. 61/447,721, filed on Mar. 1, 2011.

(51) Int. Cl.
*B01F 5/04* (2006.01)
*C07C 51/31* (2006.01)

(52) U.S. Cl.
CPC .............. *B01F 5/0463* (2013.01); *B01F 5/0456* (2013.01); *C07C 51/316* (2013.01)

(58) Field of Classification Search
CPC .................................................... B01F 5/0463
See application file for complete search history.

(56) References Cited

FOREIGN PATENT DOCUMENTS

| DE | 37 28 557 A1 | | 3/1989 |
|---|---|---|---|
| DE | 3728557 A1 | * | 3/1989 |
| DE | 1 354 866 A1 | | 10/2003 |
| DE | 10 2008 037 374 A1 | | 4/2009 |
| DE | 10 2007 054 770 A1 | | 5/2009 |
| EP | 1 467 018 A1 | | 10/2004 |
| FR | 1.211.889 | * | 3/1960 |

OTHER PUBLICATIONS

International Preliminary Report on Patentability issued Jun. 26, 2013 in PCT/EP2012/053391 (with English translation).
International Search Report Issued Jul. 31, 2012 in PCT/EP2012/053391 (with English Translation).
E. L. Paul, "Handbook of Industrial Mixing, Chapter 7: Mixing in Pipelines", John Wiley & Sons, 2004, pp. 391-452.
"Perry's Chemical Engineers Handbook", 8$^{th}$ Edition, MacGraw Hill, 2008, pp. 6-32-6-33.
Andrew W. Chen et al., "Systematic Approaches for Design of Distribution Manifolds Having the Same Per-Port Outflow", Journal of Fluids Engineering, © 2009 by ASME, Jun. 2009, vol. 131, pp. 061101-1-061101-9.
U.S. Appl. No. 13/661,652, filed Oct. 26, 2012, Leschinski, et al.
U.S. Appl. No. 13/587,378, filed Aug. 16, 2012, Mattke, et al.

* cited by examiner

*Primary Examiner* — Joseph Kosack
(74) *Attorney, Agent, or Firm* — Oblon, McClelland, Maier & Neustadt, L.L.P

(57) ABSTRACT

The subject of the present invention is an apparatus for the intermixing of a fluid stream with a fluid stream, which comprises a pipe through which the fluid stream is routed, at least two distributors for delivering the fluid stream being arranged inside the pipe, this arrangement of the distributors being made possible by bores in the casing of the pipe, and these distributors having a free flow cross section which is constant or decreases continuously, as seen in the main direction of flow of the fluid, and the distributors having one or more rows of holes for delivering the fluid into the fluid.

12 Claims, 3 Drawing Sheets

METHOD AND APPARATUS FOR THE INTERMIXING OF TWO FLUID STREAMS

The present application incorporates the provisional U.S. application 61/447,721 filed on Mar. 1, 2011 by reference.

The present invention relates to an improved apparatus for the intermixing of two fluid streams (1) and (2) and to a method for the intermixing of two fluid streams, using the apparatus according to the invention. Furthermore, it relates to an improved method for the production of adipic acid, using the apparatus according to the invention.

Numerous technical solutions for the intermixing of two fluid streams are known. Fluid streams in the context of this invention are understood in this case to mean, in general, substance streams which are present in liquid or gas form under the prevailing conditions, the prevailing conditions being capable of varying sharply in terms of the generally relevant parameters, such as pressure or temperature, on account of widely different technical applications. In this case, a fluid stream may also constitute a mixture of a plurality of different substances which are all in the same state of aggregation (liquid or gaseous). Thus, for example, liquid starting materials are admixed in continuous-throughflow reactor geometries by means of a pipe and ring distributor mounted in cross flow. Further known solutions are T-pieces, static mixers or combinations of a plurality of distributors (Paul, E. L., Handbook of Industrial Mixing, Jon Wiley & Sons, 2004, p. 391-452). DE 10 2008 037 374 A1 describes a ring distributor in which a toridal ring with holes is used in the gas burner for mixing a plurality of gas streams.

Figure 1:
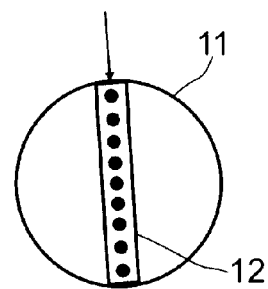
FIG. 1 shows an embodiment with a section through a pipe (11) in which is mounted a lance (12) with bores for distributing a second fluid stream.
Figure 2:
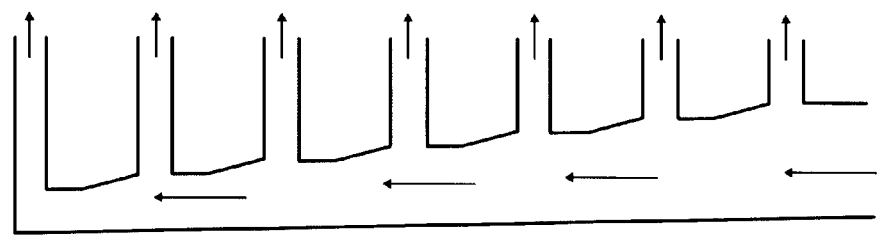
FIG. 2 shows an embodiment with discontinuous adaptation of a flow cross section in a distributor pipe to keep constant static pressure along a flow line.

If one starting material (fluid) is required in a larger quantity than the other starting materials (fluids), the starting material with the largest volume flow (designated below as fluid stream (1)) is usually supplied in a pipeline geometry to the reaction part, and the smaller starting material volume flow is then added in cross flow, for example, by means of a plugged-in pipe distributor, as illustrated diagrammatically in FIG. 1 (designated below as fluid stream (2)). What can be seen here is a section through a pipe (11) in which a lance (12) with bores for distributing the second fluid stream is mounted. Known pipe or ring distributors mostly comprise circular cross sections with one or more rows of holes for distributing the volume flow to be mixed into the main stream. In order to ensure that the liquid volume flow is apportioned uniformly to all the holes, the cross-sectional ratio of the pipe distributor to the sum of the hole areas must be sufficiently high (Perry's Chemical Engineers Handbook, 8th Edition, Mc Graw Hill, 2008, p. 6-32-6-33). Otherwise, the mass flow decreasing in the direction of flow of the distributor from hole to hole increases the static pressure in the distributor and therefore the available propulsive force for outflow from the holes. This gives rise to a preferred throughflow of the holes lying downstream, as seen in the direction of flow, as compared with holes which lie further upstream in the distributor.

Where pipe distributors are concerned, a known possibility is the discontinuous adaptation of the flow cross section in the distributor pipe, so that the static pressure remains as constant as possible along a flow line. This is illustrated in FIG. 2. The arrows symbolize the direction of flow of the fluid, and the reduction in the flow cross section in the direction of flow can be seen.

Furthermore, it is known to adapt the hole diameters, while the distributor cross-sectional area is constant, so that the hole pressure loss likewise increases in the direction of flow corresponding to the rise in static pressure in the distributor pipe. This may also be implemented in the form of a slot, the width of which is variable over the length. A further conventional alternative is to vary the length to diameter ratio of the side pipes adjoining the distributor, so that the pressure loss in the side pipes is adapted to the rise in the static pressure in the main pipe (Chen, A. W. Sparrow, E. M., Journal Fluid. Eng., Vol. 131 2009, p. 1-9).

If the fluids to be mixed participate in an exothermic reaction, as low a volume of the distributor geometry as possible is mostly advantageous. Since backflow into the distributor geometry and uncontrolled reaction of the starting materials usually cannot be prevented, it is advantageous to limit the reaction volume of the distributor as far as the next upstream safety device (for example, a non-return valve).

DE 10 2007 054 770 A1 describes an arrangement in a liquid-carrying hollow cross section, in particular a water-carrying line, in which a displacer element is installed which limits the cross section available for the liquid. The stability of the line in the event of a temperature-induced change in volume of the fluid (solidifying/freezing) is thereby to be increased.

EP 1 354 866 B1 describes a method for the production of alkane dicarbonic acid in which a mixing apparatus is used (claim 1).

However, the known intermixing apparatuses have disadvantages. Thus, undesirable inhomogenities repeatedly arise during the intermixing of the two fluids, and, in order to achieve a satisfactory distributing action, a relatively high volume-specific pressure loss has to be applied which is detrimental to the effectiveness of the mixing method. A distributing action in the context of this invention is understood to mean the width, related to the average value of the ideally fully mixed state, of the concentration distribution of the fluid emerging into another space via the distributor. Standard deviation is generally used in order to describe the width of the concentration distribution. A good distributing action denotes a state with a small width of concentration distribution at a specific location in relation to the average value of the ideally fully mixed state, that is to say a low standard deviation. In general, a standard deviation of 90-95% related to the average value is considered to be fully mixed. Depending on the mixing task even a lower standard deviation (<90%) may be sufficient for the pipe cross section with distributor. In the case of a turbulent pipe flow, additional full mixing takes place downstream of the distributor due to turbulent vortex structures and diffusion processes in the flow. The mixing task may then be considered as a two-stage process. It is composed, on the one hand, of a premixing of the fluid over the pipe cross section with the distributor and, on the other hand, of subsequent turbulent mixing in the pipe. It is known that, with good predistribution, the subsequent turbulent mixing process in the pipe flow can be improved, so that a shorter pipe extent is necessary in order to achieve good full mixing.

For good pre-mixing, the fluid emerging from the distributor should directly cover as large a fraction of the pipe cross section as possible, as seen in the radial directions.

In order to implement a lower pressure loss, it is necessary to design the known mixing apparatuses such that a volume inside the distributor is filled with the fluid (2) to be admixed, although this likewise has an adverse effect upon the mixing method.

The set object, therefore, is to find an improved apparatus for the intermixing of two fluid streams, which avoids said disadvantages and allows intermixing which is simple and effective in terms of process engineering, along with high distributing action. Furthermore, an improved method for the intermixing of two fluid streams is to be provided.

Accordingly, an apparatus for the intermixing of a fluid stream (1) with a fluid stream (2) has been found, which comprises a pipe through which the fluid stream (1) is routed, at least two distributors for delivering the fluid stream (2) being arranged inside the pipe, this arrangement of the distributors being made possible by bores in the casing of the pipe, and these distributors having a free flow cross section which, as seen in the main direction of flow of the fluid (2), is constant or decreases continuously and the distributors having one or more rows of holes for delivering the fluid (2) into the fluid (1). The inlet points of the distributors are preferably arranged in a plane perpendicular to the longitudinal axis of the pipe or, especially preferably, so as to be offset from one another at a distance of at most up to five times the pipe diameter.

By virtue of the arrangement according to the invention of at least two distributors which project radially into the pipe in which the fluid (1) is routed, a good distributing action can be achieved, along with relatively low volume-specific pressure loss. For a more detailed explanation, reference is made to FIG. 3 which illustrates by way of example an embodiment according the invention of the apparatus. What can be seen here is a section through a pipe (32) which carries the fluid (1) and into which three distributors (31) project radially, the distributors having bores through which the fluid (2) administered to the distributors is intermixed with the fluid (1) in the inner space of the pipe (32). In comparison with the apparatus illustrated in FIG. 1, when the apparatus according to the invention is in operation it is advantageously possible to achieve just as good a distributing action in the case of a lower volume-specific pressure loss or to achieve a better distributing action in the case of an identical volume-specific pressure loss, as a result of which the operation of the apparatus according to the invention proves to be markedly more effective. This marked positive effect is also attributable to the fact that, in the apparatus illustrated in FIG. 3, the three distributors are acted upon with the fluid 2 separately from outside and, because of this pro-rata apportionment of the substance stream, shorter distances through rows of holes have to be covered, with the result that it becomes possible to achieve the desired distributing action with a lower pressure loss.

The apparatus according to the invention is suitable for the intermixing of the most diverse possible fluid streams. Thus, for example, a plurality of gaseous fluids or fluids in a liquid state of aggregation can be mixed with one another. Quantity ratios in which one or more smaller fluid streams (2) are mixed into the larger fluid stream (1) via the distributor are preferred. A volume ratio of the fluid stream (2) to the fluid stream (1) of 0.001-1 is preferred. The range of 0.01-0.5 is especially preferred. Preferred substance groups are aqueous or nonaqueous inorganic or organic acids and lyes, and also short-chain, aromatic, cyclic and cycloaliphatic hydrocarbons and metal catalysts, organometallic catalysts or organic catalysts. Fluids which react with one another while at the same time releasing heat are preferred. Cyclohexane derivatives which react with oxidants so that oxidation reactions take place, with heat being generated are especially preferred. The starting materials of this reaction may already be present in one of the fluid streams. Water, hydrogen nitrate, cyclohexanol, cyclohexanone and copper and vanadium catalysts, which, with heat being generated, react together to form adipic acid and also glutaric acid and succinic acid, are especially preferred. In this case, preferably, the cyclohexanol/cyclohexanone stream is the smaller-quantity fluid stream (2) and the aqueous hydrogen nitrate stream, together with the copper and vanadium catalysts, is the larger fluid stream (1), in the quantity ratios given above.

The distributors used according to the invention have orifices through which the administered fluid (2) can emerge. These are preferably circular holes which are arranged in the form of one or more rows along the distributor. The diameter of these orifices in relation to the inlet diameter of the distributor are preferably in the range of 0.001 to 0.5, especially preferably of 0.05 to 0.2. Three to eight rows of holes are especially recommended, with the result that a further equalization of distribution can be achieved.

The free flow cross section of the distributor is understood to mean the cross-sectional area which is available to the fluid (2) when it flows through the distributor. This cross-sectional area may be constant or variable, as seen in the direction of flow of the fluid (2). A preferred embodiment of the distributor can be seen in FIG. 4. The distributor (41) here has a continuously tapering cross section (42). Furthermore, orifices (47) (holes) can be seen through which the administered fluid can flow out. A reduction in the free flow cross section can also be brought about by a displacer body mounted in the distributor. This is illustrated in FIG. 5. A distributor (51) which has a displacer body (52) on the inside can be seen here. Owing to the tapering cross section, advantageously, the rise, occurring without this measure, in the propulsive pressure difference on account of the decreasing mass flow from hole to hole is exactly compensated by the increase in velocity of the mass flow remaining in the distributor. The increase in the flow velocity in the distributor along the direction of flow can be implemented by a conical distributor without a displacer body, by a cylindrical distributor with a conical displacer body, by a conical distributor with a cylindrical displacer body or by a conical distributor with a conical displacer body. In the case of a conical distributor, a decrease in the cross-sectional area in the direction of flow is advantageous. The cross-sectional area in the distributor may preferably be annular. The displacer body may extend over the entire length or only part of the distributor. Preferably, in the case of distributors projecting into the pipe, the free flow cross sections are reduced continuously, as seen in the main direction of flow of the fluid (2), this reduction being implementable by different measures. It is recommended in this case to use distributors with a circular cross section which is preferably identical or decreasing, as seen in the main direction of flow of the fluid (2). The free flow cross section may in this case form an annular gap inside the distributors.

DEFINITIONS AND PREFERRED RANGES

The preferred embodiment of the distributor has a straight or bent geometry, in this case especially preferably also a cylindrical or conical geometry. The following definitions are made for the preferred embodiment and therefore do not explicitly describe embodiments with elliptic or rectangular cross sections.

Figure 3:
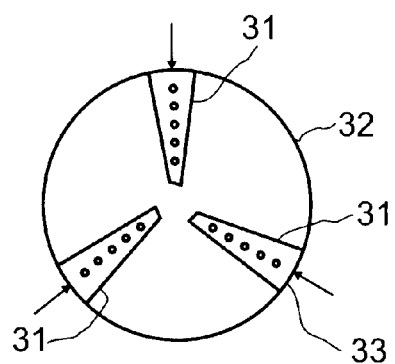
FIG. 3 shows an embodiment wherein three distributors (31) with bores project radially into a pipe (32).

The volume-specific pressure loss in the context of the present invention is understood to mean the pressure loss for the fluid stream flowing through the distributor in relation to the free volume of a cylindrical volume element on the distributor, with the following definitions:

In FIG. 3, the diameter of the distributor at the common interface of the distributor and pipe (33) is designated below by the symbol $D_0$. The associated area is designated at the inlet cross section. The included fluid volume $V_F$ is located in the distributor. The fluid volume in the distributor is defined as the volume of the fluid (2) which occupies the capacity available in the distributor, with the holes closed, as far as the inlet cross section.

The pipe (32) is illustrated in FIG. 3. The associated diameter is designated below by $D_R$. By the definition of the volume ratio, the free volume of the fluid in the main flow which is not covered by the distributor and is located in a cylindrical pipe element with a length $D_0$ and with a diameter $D_R$ is put into relation with the overall volume of the same pipe piece without a distributor.

The volume ratio $\varepsilon$ is defined as follows:

$$\varepsilon = \frac{\frac{\pi D_R^2}{4} D_0 - V_F}{\frac{\pi D_R^2}{4} D_0}$$

To describe advantageous geometries and the volume-specific pressure loss, the dimensionless characteristic number DPV is defined as:

$$DPV = \frac{\zeta}{\varepsilon}.$$

Pressure loss $$\Delta p_v = \zeta \frac{\rho}{2} v^2$$

Density of fluid (2)      $\rho$

Pressure loss coefficient      $\zeta$

Velocity of fluid (2) in the inlet cross section      $v$

With apportionment of the volume flow to all the holes being the same, a distributor is advantageous when the value of DPV is low. In a distributor with a low DPV value, the energy required for the uniform apportionment of the volume flow to the individual holes of the distributor in relation to the free volume of the distributor is utilized more effectively than in a distributor with a higher DPV value.

In the distributor illustrated in FIG. 4, the length between the margin of the inlet cross section (43) and the end of the distributor (44) is illustrated and is designated below by $L_1$. $L_M$ is the distributor length standardized with the pipe diameter:

$$L_M = \frac{L_1}{D_R}$$

The preferred length of the distributor in relation to the pipe diameter is 0.05 to 1, especially preferably 0.1 to 0.5.

$D_{0,M}$ is the distributor diameter, standardized with the pipe diameter, in the inlet cross section.

$$D_{0,M} = \frac{D_0}{D_R}$$

The preferred standardized diameter of the distributor in relation to the pipe diameter is from 0.005 to 0.5, especially preferably from 0.01 to 0.2.

Figure 4:
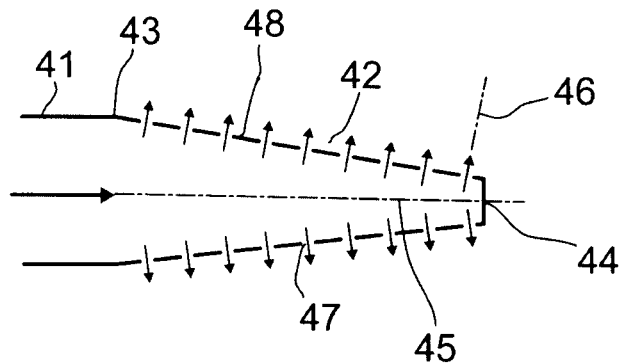
FIG. 4 shows an embodiment of the distributor (41) with a continuously tapering cross section (42) and orifaces (47).
Figure 5:
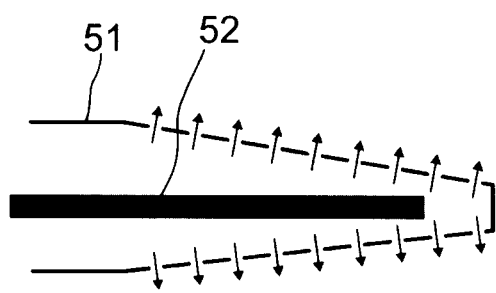
FIG. 5 shows an embodiment with a distributor (51) which has a displacer body (52) on the inside.

The diameter of the distributor end (44) illustrated in FIG. 4 is designated below by $D_1$. The dimensionless cone/diameter ratio is the ratio of the end diameter to the inlet diameter at the distributor start (43):

$$D_{1,M} = \frac{D_1}{D_0}$$

The preferred cone/diameter ratio of the distributor is 0 to 1, especially preferably 0.25 to 1.

Figure 7:
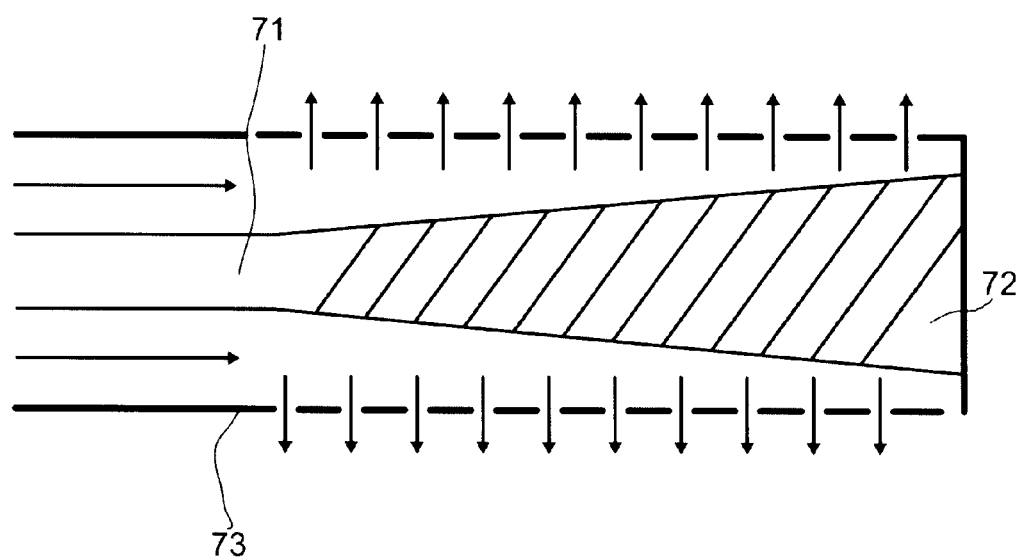
FIG. 7 shows an embodiment with a displacer body (71) in a distributor (73).

In the distributor illustrated in FIG. 7, a displacer body (71) is provided. This has the diameter $D_{0,K}$ at the inlet cross section of the distributor (73). The diameter at the end (72) of the displacer body is designated by $D_{1,K}$. The length between the start (73) and end (72) is designated by $L_{1,K}$. The standardized displacer body length is $$L_K = \frac{L_{1,K}}{L_1}$$

The preferred displacer body length is from 0.1 to 1, especially preferably from 0.3 to 1.

$D_{0,K}$ is the outside diameter of the displacer body in the inlet cross section. $D_{KM}$ is the diameter ratio of the displacer body and distributor:

$$D_{KM} = \frac{D_{0,K}}{D_0}$$

The preferred diameter ratio of the displacer body and distributor is from 0 to 0.95, especially preferably from 0 to 0.7.

$D_{1,K}$ is the diameter of the displacer body at the end furthest away from the inlet cross section. The standardized diameter ratio of the displacer body is:

$$D_K = \frac{D_{0,K}}{D_{1,K}}$$

The displacer body diameter ratio is preferably from 0.1 to 1, especially preferably from 0.3 to 1.

A conical form of the distributor is especially preferred. In this case, especially preferably, a cylindrical displacer body may be present in the flow cross section upstream of the inlet cross section into the distributor. Moreover, a cylindrical distributor geometry with a conical displacer body, in which, as illustrated in FIG. 7, the end diameter (72) is larger than the start diameter (71), is especially preferred.

In a preferred embodiment, the inlet points in the distributors into the pipe are arranged within a plane perpendicular to the longitudinal axis of the pipe. This variant can be seen, for example, in FIG. 3. Inlet points are to be understood in this case as meaning the area centers of gravity of the cross-sectional areas of the distributors, level with the surface area of the pipe (32). In the case of the distributors illustrated here, with a circular cross-sectional area, the area center of gravity is located, for example, at the center of this circular area, and the sum of these area centers of gravity therefore lies on the longitudinal mid-axis through the distributor, as formed by a prolongation of the sketched arrows into the distributor. The inlet point therefore lies at the interface of this axis with the surface area (32) of the pipe, and the three inlet points illustrated here in FIG. 3 lie in one plane. As a result of the arrangement in one plane, the distributors are in direct proximity, and rapid and effective intermixing over the entire cross section of the pipe (32) in a short time can thereby be ensured. This effect is especially pronounced when the inlet points of the distributors or the distributors into the pipe are actually arranged within a plane perpendicular to the longitudinal axis of the pipe. However, a certain "offset" also leads to very good results and therefore, according to this invention, inlet points which are displaced with respect to the longitudinal axis of the pipe (32) by up to 1.5 times the hydraulic diameter of the pipe (32) on the longitudinal axis are also covered by this invention as "lying in one plane". A hydraulic diameter in this case is understood to mean the quotient of four times the flow cross section and the circumference wetted by the fluid. In the case of a circular pipe (32), the hydraulic diameter corresponds to the pipe diameter. For other geometries of the pipe (32), such as, for example, ducts with a rectangular cross section, the hydraulic diameter can easily be determined.

As illustrated, for example, in FIG. 3, the distributors according to the invention project into the pipe (32). This principle affords advantages, as compared with known ring distributors, because, for example, they can be introduced simply into the pipe by means of connection pieces. Mounting which is easy in terms of process engineering, maintenance and also retrofitting are therefore possible. Preferably, three to five distributors project into the pipe, preferably at least one distributor having a displacement body inside it.

In order to ensure effective and uniform distribution, three to five distributors are especially recommended. It is especially recommended to arrange these so as to be distributed uniformly over the circumference of the pipe in order to further increase the uniformity of full mixing.

The holes provided in the distributor for distributing the fluid (2) may be of circular, elliptic or rectangular design or be designed in the form of a slot.

As illustrated in FIG. 4 the hole spacing (48) is introduced as the center spacing of two adjacent orifices (47). It is standardized below with the hole diameter and is designated by the variable $s_L$. For round holes, the length ratio $s_L$ arising from the hole spacing and the hole diameter preferably lies between 0.1 and 10, especially preferably between 0.2 and 1.5.

The mid-axis of the distributor (45) and the mid-axis of a hole (46) are illustrated in FIG. 4. The hole mid-axis (46) may be arranged in the normal direction to the mid-axis of the distributor (44) or may deviate from this by the amount of a specific angle of inclination, referred to below by the designation $\alpha_L$. The angle formed between the mid-axis (45) and the mid-axis (46) preferably lies between 90 and 300°, especially preferably between 90 and 70°.

In relation to the diameter $D_0$ of the distributor, the hole diameter preferably lies between 0.01 and 0.5, especially preferably between 0.05 and 0.2. Especially preferred are holes with a circular cross section or at least one slot of the same area, arranged along the longitudinal axis, with the same cross-sectional area distribution as a function of the length spacing from the inlet cross section as in the case of an arrangement with holes. The hole diameter may preferably vary within a row of holes along at least one distributor, as seen in the main direction of flow of the fluid (2). A variation is preferred in which the hole diameter of a hole in relation to the hole diameter of the next upstream directly adjacent hole varies at most by the factor 0.5-1.5 and especially preferably the factor 0.8-1.2.

As explained above, the inlet points of the distributors lie in one plane in the way defined according to the invention. As illustrated in FIG. 3, the distributors can then project linearly into the pipe (32) with respect to their longitudinal axis.

Figure 6:
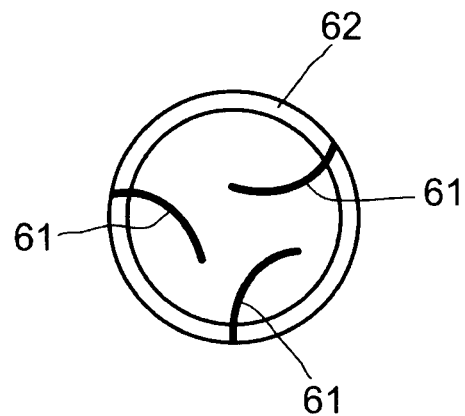
FIG. 6 shows an embodiment in which distributors (61) projecting into a pipe (62) have a bent geometry.

A further preferred embodiment is illustrated in FIG. 6. Here, the distributors (61) projecting into the pipe (62) have a bent geometry, in an especially preferred embodiment the curvature of the distributors being configured in such a way that, in terms of the above-defined characteristic variable (area center of gravity), they are arranged over the entire circumference, that is to say not only in relation to the inlet point into the pipe (62), in a plane perpendicular to the longitudinal axis of the pipe (62).

Preferably, the distributors, like the pipe into which they project, have a circular cross section. However, other geometries, such as, for example, rectangular cross sections, or other forms may also be used.

The apparatus according to the invention has, as compared with the prior art, a lower volume-specific pressure loss or, with the definitions made, a lower DPV value.

The apparatus according to the invention affords an effective way, simple in terms of process engineering, of intermixing two or more fluids. A high distributing action and good full mixing, along with relatively low volume-specific pressure losses, can be implemented here. The apparatus can advantageously be easily mounted and maintained.

EXAMPLES

A non-inventive apparatus according the known prior art and an apparatus according to the invention are compared with one another. The same quantity and the same fluid are supplied to both apparatuses. In this case, the following design criteria are taken as a basis in order to ensure comparability of the apparatuses in terms of the mixing action: the dimensionless length $L_M$, the number of holes, the hole spacing and the diameter of the inlet cross section $D_0$ are identical for both apparatuses. Erroneous distribution during the flow in the distributor and the apportionment of the overall volume flow to the individual holes is defined as being the deviation from the ideal state of apportionment in which the volume flow through each hole is identical. For good comparability of the mixing members considered here, the erroneous distribution to the individual holes should likewise be identical. This is calculated according to the existing and generally known prior art (Perry's Chemical Engineers Handbook, 8th Edition, Mc Graw Hill, 2008, p. 6-32-6-33) and is stipulated at 5%. The hole diameter is fixed on the basis of this. The non-inventive apparatus, designated below as variant (1), posses a cylindrical form without further fittings. The apparatus according to the invention, designated below as variant (2), possesses a cylindrical outer form and a conical displacer body. Both apparatuses have in each case four rows of holes distributed over the circumference and 31 holes per row of holes. It is assumed for both variants that in each case three apparatuses are introduced radially into the fluid stream (1). It can be seen in the tabulated results that, with the mixing action being the same, variant (2) is more advantageous in terms of the DPV value, since the latter is lower. since the latter is lower.

| Geometry definitions | Variant (1) | Variant (2) | |
|---|---|---|---|
| $L_M$ | 0.5 | 0.5 | [—] |
| $D_{0,M}$ | 0.05625 | 0.05625 | [—] |
| $D_{1,M}$ | — | 1 | [—] |
| $L_K$ | 1 | 1 | [—] |
| $D_{KM}$ | — | 0.556 | [—] |
| $D_K$ | — | 0.667 | [—] |
| Standardized hole diameter | 0.0588 | 0.0806 | [—] |
| Angle $\alpha_L$ | 90° | 90° | ° |
| Spacing $s_L$ | 1.97 | 1.78 | [—] |
| $\epsilon$ | 0.9873 | 0.9935 | [—] |
| $\zeta$ | 10.1 | 3.1 | [—] |
| DPV | 10.2 | 3.1 | [—] |

Definition and scope of validity of the example:

Using the viscosity η of the fluid, the density ρ of the fluid, the inlet diameter $D_0$ of the distributor and the associated inlet velocity uo in the inlet cross section, the Reynolds' number Re is defined as follows:

$$Re = \frac{\rho u_0 D_0}{\eta}.$$

The above example is valid for a range of use for the distributor with a Reynolds number Re higher than 2300.

The invention claimed is:

1. An apparatus for intermixing of a fluid stream (1) with a fluid stream (2), the apparatus comprising;
   a pipe through which the fluid stream (1) is routed; and
   at least two distributors for delivering the fluid stream (2), wherein:
   the at least two distributors are arranged inside the pipe, such that the arrangement of the distributors is made possible by bores in the casing of the pipe;
   the at least two distributors have a free flow cross section which, as seen in a main direction of flow of the fluid (2), is constant or decreases continuously;
   the at least two distributors have one or more rows of holes for delivering the fluid (2) into the fluid (1); and
   the apparatus comprises at least one distributor which has a displacement body inside of it.

2. The apparatus according to claim 1, wherein inlet points of the distributors into the pipe are arranged within a plane perpendicular to the longitudinal axis of the pipe.

3. The apparatus according to claim 2, wherein the distributors are arranged within a plane perpendicular to the longitudinal axis of the pipe.

4. The apparatus according to claim 1, wherein the distributors which project into the pipe have a continuous reduction in a free flow cross section, as seen in the main direction of flow of the fluid (2).

5. The apparatus according to claim 1, comprising three to five distributors which project into the pipe.

6. The apparatus according to claim 1, comprising at least one distributor in which diameters of the holes are varied within a row of holes, as seen in the main direction of flow of the fluid (2).

7. The apparatus according to claim 1, wherein the distributors have a bent geometry, as seen in the main direction of flow of the fluid (2).

8. The apparatus according to claim 1, wherein the distributors have a circular cross section which is identical or decreasing, as seen in the main direction of flow of the fluid (2).

9. The apparatus according to claim 1, wherein the pipe has a circular cross section.

10. The apparatus according to claim 1, wherein a free flow cross section within the distributors forms an annular gap.

11. A method for intermixing of two fluid streams (1) and (2), the method comprising passing the two fluid streams into the apparatus of claim 1.

12. A method for producing adipic acid, the method comprising intermixing a fluid stream (1) comprising a catalyst-enriched aqueous hydrogen nitrate, and a fluid stream (2) comprising cyclohexanol and cyclohexanone, wherein the intermixing occurs in the apparatus of claim 1.

* * * * *